United States Patent
Shi

(10) Patent No.: US 7,981,131 B2
(45) Date of Patent: Jul. 19, 2011

(54) DISPOSABLE SINGLE-SWING-ARM INCISION SAFETY LANCET

(76) Inventor: Guoping Shi, Suzhou (CN)

( * ) Notice: Subject to any disclaimer, the term of this patent is extended or adjusted under 35 U.S.C. 154(b) by 420 days.

(21) Appl. No.: 12/289,201

(22) Filed: Oct. 22, 2008

(65) Prior Publication Data

US 2010/0010528 A1    Jan. 14, 2010

(30) Foreign Application Priority Data

Jul. 9, 2008    (CN) .......................... 2008 1 0023018

(51) Int. Cl.
  *A61B 5/151* (2006.01)
(52) U.S. Cl. ....................................... 606/182; 606/185
(58) Field of Classification Search .................. 600/573, 600/583; 604/131, 134; 606/117, 181–189
  See application file for complete search history.

(56) References Cited

U.S. PATENT DOCUMENTS

| | | | | |
|---|---|---|---|---|
| 4,628,929 A | * | 12/1986 | Intengan et al. | 606/182 |
| 5,133,730 A | | 7/1992 | Biro et al. | |
| 5,314,441 A | * | 5/1994 | Cusack et al. | 606/182 |
| 5,571,132 A | * | 11/1996 | Mawhirt et al. | 606/182 |
| 5,645,555 A | * | 7/1997 | Davis et al. | 606/182 |
| 5,772,677 A | * | 6/1998 | Mawhirt et al. | 606/181 |
| 5,797,940 A | * | 8/1998 | Mawhirt et al. | 606/167 |
| 6,221,089 B1 | * | 4/2001 | Mawhirt | 606/181 |
| 7,704,265 B2 | * | 4/2010 | Schraga | 606/182 |

* cited by examiner

*Primary Examiner* — Corrine M McDermott
*Assistant Examiner* — Rachel S Papeika
(74) *Attorney, Agent, or Firm* — Oliff & Berridge, PLC

(57) ABSTRACT

A disposable single-swing-arm incision safety lancet is provided, which includes a casing (2) and a trigger. It is characterized in that the casing (2) is provided inside with an incision blood-taking mechanism composed of a cam (3), a swing arm (4), a blade (1) and a spring (8). In the incision blood-taking mechanism of the present invention, the cam, being driven to rotate under elastic force of the spring, pushes via the curved surface against the swing arm, which thus swings with the third radius R3 as the radius. The point of the blade 1 is swingingly stretched out of the casing 2 from the blood-taking opening 5 along the arc-shaped path A, thus producing the incising action. The present invention is novel in structure, clever in concept, and reliable in working. Since the movement of the incision blood-taking mechanism is controlled by the spring, the action strength can be controlled through the design of elastic force of the spring. Therefore, the mechanism possesses higher accuracy and controllability compared with the prior art, resolving the existing technical problems on this aspect.

3 Claims, 4 Drawing Sheets

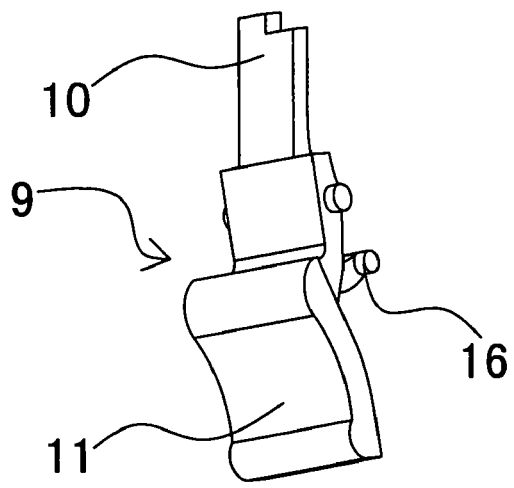
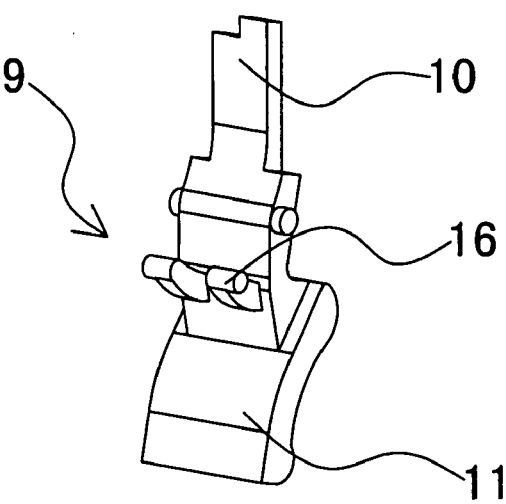
Fig. 5　　　Fig. 6
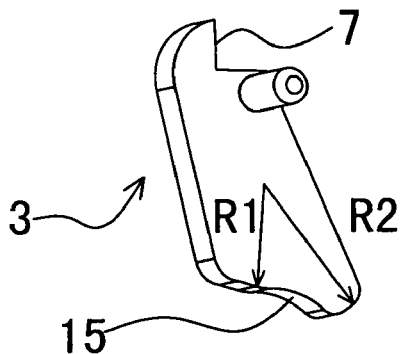
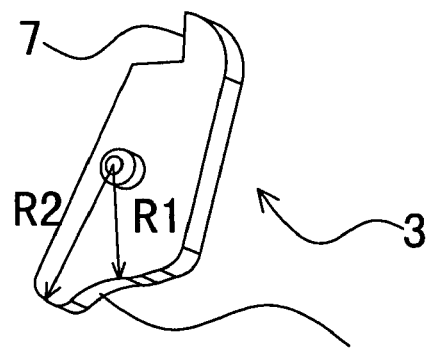
Fig. 7　　　Fig. 8
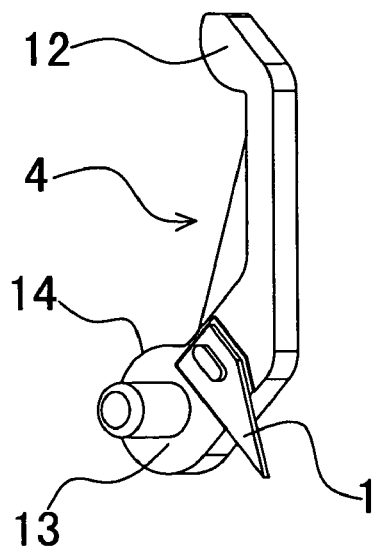
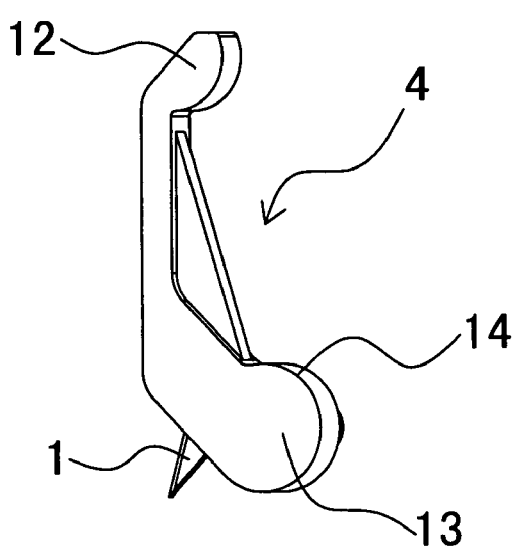
Fig. 9　　　Fig. 10

DISPOSABLE SINGLE-SWING-ARM INCISION SAFETY LANCET

FIELD OF THE INVENTION

Belonging to the field of medical apparatus and instruments, the present invention relates particularly to a medical safety lancet, and more particularly to A disposable single-swing-arm incision safety lancet. Such a safety lancet acts on the blood-taking site of the human body by means of incision of the swing blade, mainly used for taking blood from a human finger and other body parts as well.

BACKGROUND OF THE INVENTION

The safety lancet is widely used in various medical units as a medical instrument for taking blood from the human body. The existing lancets can be divided into a puncture lancet and an incision lancet according to the different blood-taking methods. The puncture lancet acts on the blood-taking site by means of acupuncture, mainly used for taking blood from an adult's finger. The incision lancet acts on the blood-taking site by means of blade incision. The incision lancet feels less painful than the acupuncture lancet, and can take enough amount of blood, and therefore it is of a high-level product in various kinds of lancets.

American U.S. Pat. No. 5,133,730 discloses a disposable finger blood-taking device. Such a blood-taking device uses a blade, and realizes the blood-taking purpose by incising the blood-taking site with an incising action. The incising action is performed mainly as below: A button is used to push a first swing arm to swing, which again pushes a second swing arm to swing, which forces a blade on the second swing arm to stretch out of a casing to perform the incising movement; and then the first swing arm pushes the second one to make the blade be retracted into the casing. Being different from a traditional lancet where a sharp needle is pierced into the finger, such a blood-taking device uses a minute blade to incise into the finger, substituting a surgical incising action for the acupuncture action, touching capillaries and small vessels in the finger with the minimum wound and at the most effective depth, reducing damage to the cellular tissues to the utmost, making a patient suffer much less than with the traditional lancet according to tests, barely resulting in discomfort even for the youngest patient. However, such an incision blood-taking mechanism directly makes use of manual push to perform the incising action, and therefore there is a certain requirement on control of the push strength, which brings inconvenience to a user. Therefor, a problem that the present invention emphasizingly studies is how to design a new incision blood-taking mechanism, so as to overcome such a shortcoming.

CONTENTS OF THE INVENTION

Aiming at meeting the requirement on strength control by designing a new incision blood-taking mechanism, the present invention provides a disposable single-swing-arm incision safety lancet, so as to resolve the existing technical problems on this aspect.

In order to attain the above-mentioned purpose, a technical solution of the present invention is as below: A disposable single-swing-arm incision safety lancet is provided, which includes a casing and a trigger. It is innovative on the following aspects: The casing is provided inside with an incision blood-taking mechanism composed of a cam, a swing arm, a blade and a spring, where:

the cam is rotatably fixed in the casing via a pivot; the spring, as a driving element of the incision blood-taking mechanism, is positioned between the cam and the casing, and acts on the rotary direction of the cam; the trigger, as a triggering control member of the incision blood-taking mechanism, is positioned on the casing; in a pre-triggering state, an action portion of the trigger is propped against a lock gate provided on the cam, and forces the spring to be in an energy storage state, with a triggering portion of the trigger being stretched out of the casing;

the swing arm is provided with a locating end and a swing end, the locating end being positioned in the casing, the swing end being hung in the casing; the blade is fixedly mounted on the swing end, which is further provided with a working face, which is contactively matched with flange of the cam; the flange of the cam is provided, corresponding to this working face, with a curved surface, whose curvature radius is transient from a first radius R1 to a second radius R2; this curved surface forces the swing arm to swing with rotation of the cam, with the distance from center of the locating end itself to the point of the blade as a third radius R3;

the blade is located at a blood-taking opening provided on the casing; when the incision blood-taking mechanism swings, the point of the blade is swingingly stretched out of the casing from the blood-taking opening along an arc-shaped path A; when the curved surface on the cam is rotated past the working face on the swing arm, the swing arm, by means of the self flexibility, makes the point of the blade swing back to inside the casing along the arc-shaped path A.

The explanation for the relevant contents of the above technical solution is as below:

1. In the above solution, the "spring" is the driving element of the incision blood-taking mechanism, and can specifically be selected from the group consisting of a tension spring, a compression spring, a torsion spring and a flat spring. Various kinds of spring can be selected to drive the cam to rotate after the connection relation among each part of the incision blood-taking mechanism has been determined.

2. In the above solution, the "trigger" is the triggering control member of the incision blood-taking mechanism, and the incision blood-taking mechanism is driven to perform the incision blood-taking action by means of triggering the control member. The following two kinds of structures are adopted for the trigger (however, other structures can also be adopted):

(1) A push structure, composed of a lever button rotatably located on the casing; the front end of the button is an action portion, and the rear end the triggering portion, with a protection block being clipped as a safety structure between the triggering portion and the casing; and (2) a pushingly-triggered structure, composed of a pushingly-triggered key slidely located on the casing; the front end of the pushingly-triggered key is the action portion, and the rear end the triggering portion, with a protection sleeve being clipped as a safety structure between the triggering portion and the casing.

The designing concept of the present invention is as below: The swing arm is pushed to swing with the third radius R3 as the radius by means of the curved surface of the flange of the cam mechanism, making the point of the blade be stretched out of the casing from the blood-taking opening along the track of the arc-shaped path A; when the curved surface on the cam is rotated past the working face on the swing arm, the swing arm, by means of the self flexibility, makes the point of the blade swing back to inside the casing along the arc-shaped path A. The distance between the extreme outer end of the arc-shaped path A and the blood-taking opening of the casing is the incision depth H, and the width of the arc-shaped path A exceeding the blood-taking opening the incision width W. The incision depth H is dependent on the difference between the second radius R2 and the first radius R1 of the curved surface of the flange of the cam, i.e. R2−R1=incision depth H+reserved distance for the point of the blade in the casing; the incision width W is controlled by the swing radius of the swing arm (the third radius R3). An incision of different blood-taking depth and blood-taking width can be designed by changing the dimension of R1~R3.

Because of application of the above technical solution, the present invention has the following advantages and effects compared with the prior art:

1. The present invention combines the cam, the swing arm and the spring into the single-swing-arm incision blood-taking mechanism, thus making the point of the blade go along the arc-shaped path A as the incision track; such a single-swing-arm design not only is novel in structure, clever in concept, and reliable in working, but also has outstanding substantial characteristics and technical improvement compared with the prior art.

2. For the incision blood-taking mechanism of the safety lancet of the present invention, an incision of different blood-taking depth and different blood-taking width can be designed by means of changing the dimension of R1~R3, which better meets the requirement on controlling incision depth and incision width.

3. In the incision blood-taking mechanism of the present invention, the cam, being driven to rotate under elastic force of the spring, pushes via the curved surface against the swing arm to make it swing, thus producing the incising action. It can be seen from this that movement of the mechanism is controlled by the spring, and therefore the action strength can be controlled through the design of elastic force of the spring. Therefore, the mechanism possesses higher accuracy and controllability compared with the prior art, resolving the existing technical problems on this aspect.

BRIEF DESCRIPTION OF THE DRAWINGS

FIG. 5 is a stereoscopic diagram (a) of the button according to the embodiment of the present invention;

FIG. 6 is a stereoscopic diagram (b) of the button according to the embodiment of the present invention;

FIG. 7 is a stereoscopic diagram (a) of the cam according to the embodiment of the present invention;

FIG. 8 is a stereoscopic diagram (b) of the cam according to the embodiment of the present invention;

FIG. 9 is a stereoscopic diagram (a) of the swing arm and the blade according to the embodiment of the present invention; and FIG. 10 is a stereoscopic diagram (b) of the swing arm and the blade according to the embodiment of the present invention.

In the figures above: 1. Blade; 2. casing; 3. cam; 4. swing arm; 5. blood-taking opening; 6. pivot; 7. lock gate; 8. spring; 9. button; 10. action portion; 11. triggering portion; 12. locating end; 13. swing end; 14. working face; 15. curved surface; 16. protection block; R1. the first radius; R2. the second radius; R3. the third radius; A. the first arc-shaped path; H. incision depth; and W. incision width.

DETAILED DESCRIPTION OF THE EMBODIMENTS

The present invention will be further described below with reference to drawings and embodiments.

Embodiment

A Disposable Single-Swing-Arm Incision Safety Lancet

Figure 1:
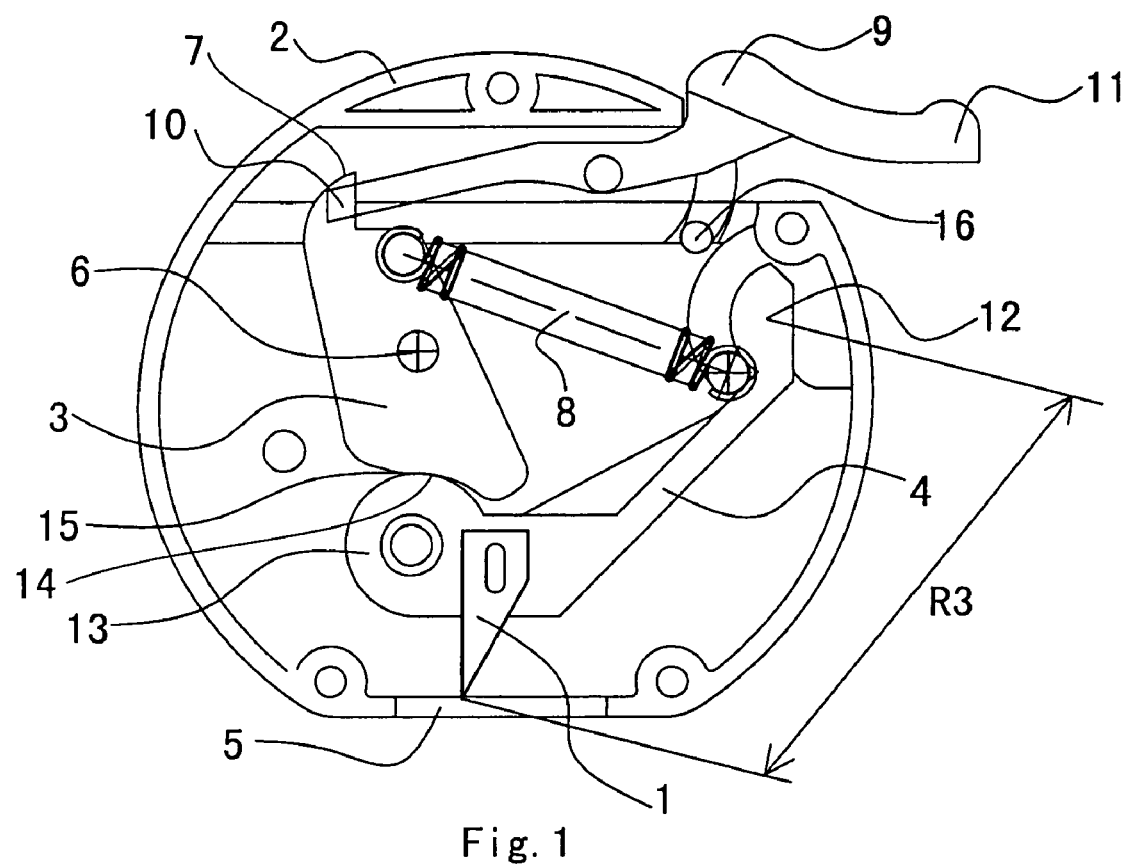
FIG. 1 is a schematic view of the pre-projection state according to the embodiment of the present invention.
Figure 2:
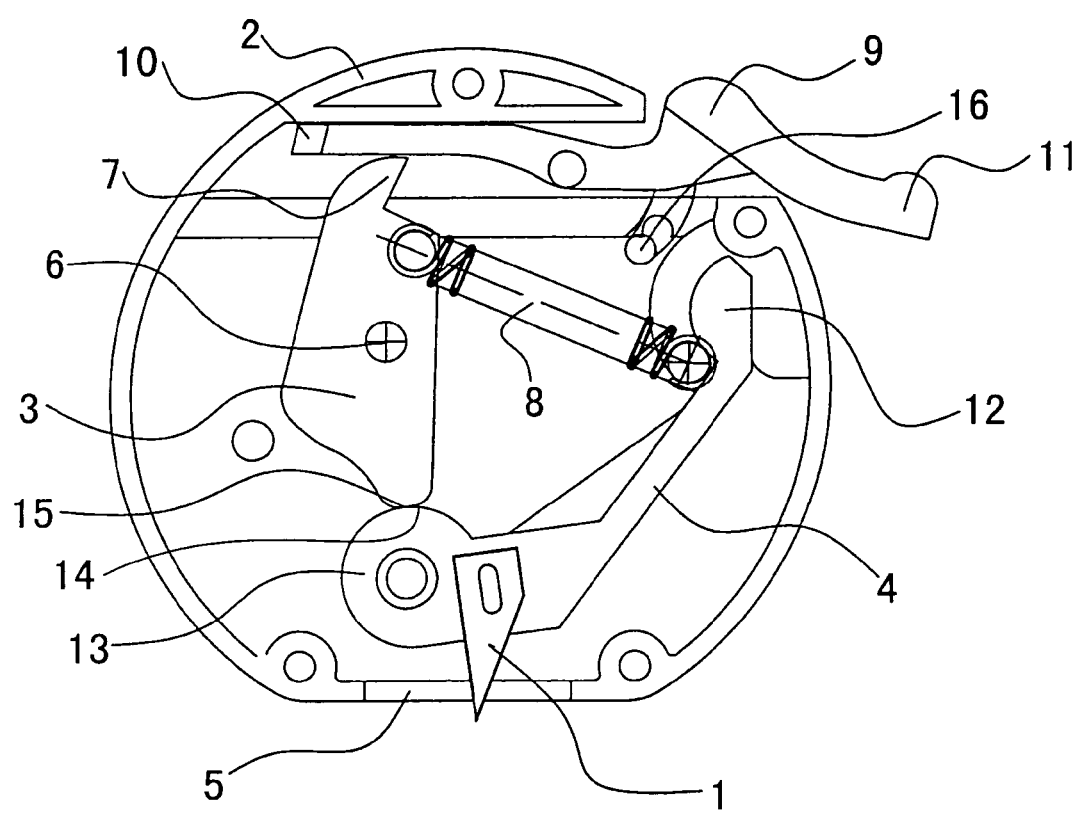
FIG. 2 is a schematic view of the state during projection according to the embodiment of the present invention.
Figure 3:
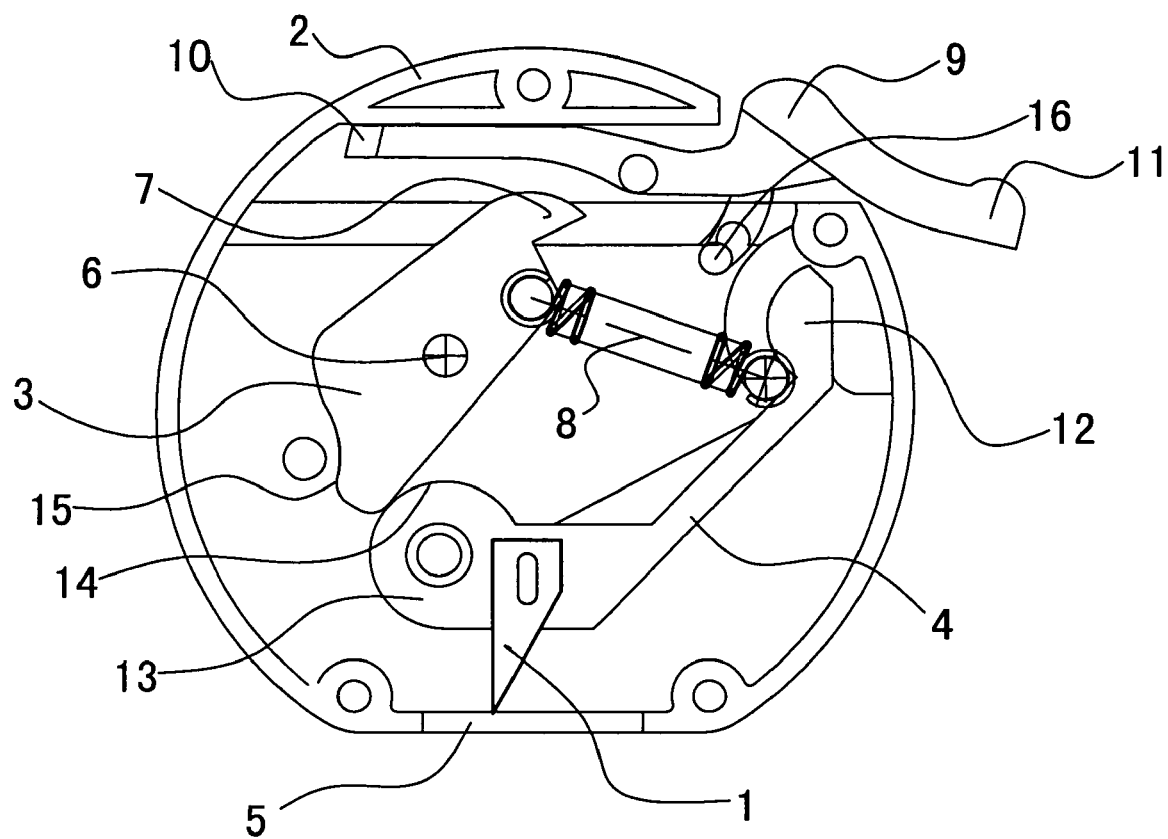
FIG. 3 is a schematic view of the post-projection state according to the embodiment of the present invention.

As shown in FIGS. 1~3, this incision safety lancet includes the casing 2, the trigger, and the blood-taking mechanism provided in the casing 2. The casing 2 is composed of two half casings, an upper cover and a lower cover. The trigger is of a push structure, which is composed of the lever button 9 rotatably located on the casing 2. Structure of the button 9 is as shown in FIGS. 5 and 6, whose front end is the action portion 10 and the rear end the triggering portion 11, with the protection block 16 being clipped as a safety structure between the triggering portion 11 and the casing 2. This protection block 16 is clipped in the bayonet of the casing 2 in the safety state (as shown in FIG. 1), with the state of this protection block 16 escaping from the bayonet being shown in FIG. 2.

The incision blood-taking mechanism is composed of the cam 3, the swing arm 4, the blade 1 and the spring 8. The structure of the cam 3 is shown in FIGS. 7 and 8, and the structure of the swing arm 4 in FIGS. 9 and 10.

As shown in FIGS. 1~3, structure of and interconnection among all the parts of the incision blood-taking mechanism are as below:

The cam 3 is rotatably fixed in the casing 2 via the pivot 6. The spring (8) (a tension spring is adopted in FIGS. 1~3), as a driving element of the incision blood-taking mechanism, is positioned between the cam 3 and the casing 2, and acts on the rotary direction of the cam 3. The button 9, as a triggering control member of the incision blood-taking mechanism, is positioned on the casing 2. In the pre-triggering state, the action portion 10 of the button 9 is propped against the lock gate 7 provided on the cam 3, and forces the spring 8 to be in the energy storage state, with the triggering portion 11 of the button 9 being stretched out of the casing 2. The protection block 16 is clipped as a safety structure between the triggering portion 11 and the casing 2, so as to prevent the incision blood-taking mechanism from being unintentionally driven.

The swing arm 4 is provided with the locating end 12 and the swing end 13, the locating end 12 being positioned in the casing 2, the swing end 13 being hung in the casing 2. The blade 1 is fixedly mounted on the swing end 13, which is further provided with the working face 14, which is contactively matched with flange of the cam 3. The flange of the cam 3 is provided, corresponding to this working face 14, with the curved surface 15, whose curvature radius is transient from the first radius R1 to the second radius R2. This curved surface 15 forces the swing arm 4 to swing with rotation of the cam 3, with the distance from center of the locating end 12 itself to the point of the blade 1 as the third radius R3.

Figure 4:
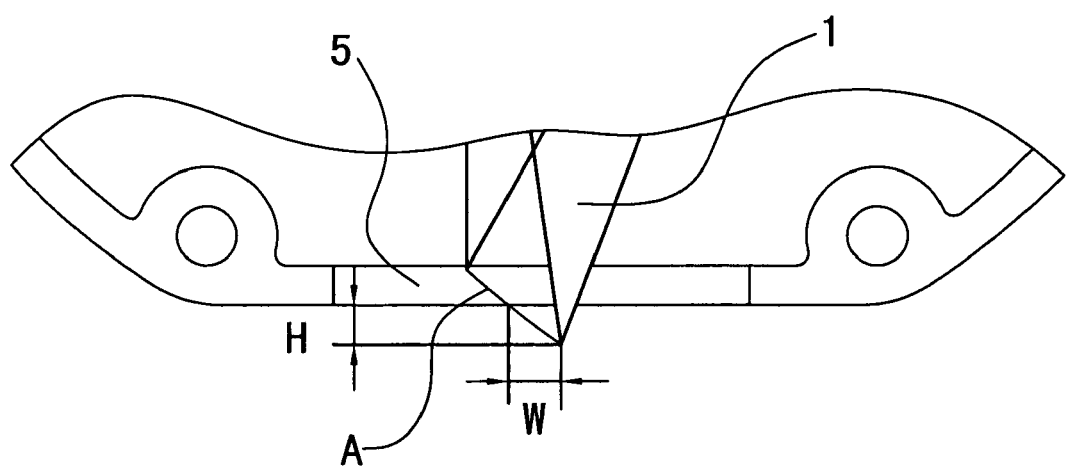
FIG. 4 is a diagram of the movement track of the point of the blade during projection according to the embodiment of the present invention.

As shown in FIG. 4, the blade 1 is located at the blood-taking opening 5 provided on the casing 2. When the safety lancet is used, the triggering portion 11 is pushed by hand, making the action portion 10 of the button 9 escape from the lock gate 7 of the cam 3 and be in the state shown in FIG. 2. Here, the spring 8 (a tension spring) pulls the cam 3 to rotate round the center of the pivot 6; the curved surface 15 of the cam 3, with rotation of the cam 3, forces the swing arm 4 to swing with the third radius R3 as the radius; the point of the blade 1 is swingingly stretched out of the casing 2 from the blood-taking opening 5 along the arc-shaped path A, thus producing the incising action. When the curved surface 15 on the cam 3 is rotated past the working face 14 on the swing arm 4, the swing arm 4, by means of the self flexibility, makes the point of the blade 1 swing back to inside the casing 2 along the arc-shaped path A.

In this embodiment, the trigger can also be of a pushingly-triggered structure (not shown in the figures) instead. For example, the trigger is composed of a pushingly-triggered key slidely located on the casing 2, with the front end of the pushingly-triggered key being the action portion 10 and the rear end the triggering portion 11; a protection sleeve is clipped as a safety structure between the triggering portion 11 and the casing 2. While in use, first the protection sleeve is extracted, and then the triggering portion 11 is pushed, making the action portion 10 escape from the lock gate 7 of the cam 3 and enter the projection state.

The above embodiment is used only for explaining the technical concept and characteristics of the present invention. It is provided to make those skilled in the art understand the present invention and implement it, and cannot thereby limit the extent of protection of the present invention. All equivalent changes or modifications according to the spirit of the present invention should fall within the extent of protection of the present invention.

What is claimed is:

1. A disposable single-swing-arm incision safety lancet, comprising:
    a casing (2) and a trigger;
    wherein:
    the casing (2) is provided inside with an incision blood-taking mechanism composed of a cam (3), a swing arm (4), a blade (1) and a spring (8);
    the cam (3) is rotatably fixed in the casing (2) via a pivot (6); the spring (8), as a driving element of the incision blood-taking mechanism, is positioned between the cam (3) and the casing (2), and acts on the rotary direction of the cam (3); the trigger, as a triggering control member of the incision blood-taking mechanism, is positioned on the casing (2); in a pre-triggering state, an action portion (10) of the trigger is propped against a lock gate (7) provided on the cam (3), and forces the spring (8) to be in an energy storage state, with a triggering portion (11) of the trigger being stretched out of the casing (2);
    the swing arm (4) is provided with a locating end (12) and a swing end (13), the locating end (12) being positioned in the casing (2), the swing end (13) being hung in the casing (2); the blade (1) is fixedly mounted on the swing end (13), which is further provided with a working face (14), which is contactively matched with flange of the cam (3); the flange of the cam (3) is provided, corresponding to this working face (14), with a curved surface (15), whose curvature radius is transient from a first radius (R1) to a second radius (R2); this curved surface (15) forces the swing arm (4) to swing with rotation of the cam (3), with the distance from center of the locating end (12) itself to the point of the blade (1) as a third radius (R3);
    the blade (1) is located at a blood-taking opening (5) provided on the casing (2); when the incision blood-taking mechanism swings, the point of the blade (1) is swingingly stretched out of the casing (2) from the blood-taking opening (5) along an arc-shaped path (A); when the curved surface (15) on the cam (3) is rotated past the working face (14) on the swing arm (4), the swing arm (4), by means of the self flexibility, makes the point of the blade (1) swing back to inside the casing (2) along the arc-shaped path (A).

2. The disposable single-swing-arm incision safety lancet according to claim 1, wherein the trigger is of a push structure, and composed of a lever button (9) rotatably located on the casing (2); the front end of the button (9) is an action portion (10), and the rear end a triggering portion (11), with a protection block (16) being clipped as a safety structure between the triggering portion (11) and the casing (2).

3. The disposable single-swing-arm incision safety lancet according to claim 1, wherein the trigger is of a pushingly-triggered structure, and composed of a pushingly-triggered key slidely located on the casing (2); the front end of the pushingly-triggered key is the action portion (10), and the rear end the triggering portion (11), with a protection sleeve being clipped as a safety structure between the triggering portion (11) and the casing (2).

* * * * *